United States Patent
Rein et al.

(10) Patent No.: US 9,786,406 B2
(45) Date of Patent: Oct. 10, 2017

(54) CELLULOSE CAPSULES

(71) Applicant: TECHNION RESEARCH & DEVELOPMENT FOUNDATION LTD., Haifa (IL)

(72) Inventors: Dmitry Rein, Nesher (IL); Yachin Cohen, Haifa (IL)

(73) Assignee: Technion Research & Development Foundation Ltd., Haifa (IL)

(*) Notice: Subject to any disclaimer, the term of this patent is extended or adjusted under 35 U.S.C. 154(b) by 162 days.

(21) Appl. No.: 14/402,367

(22) PCT Filed: May 19, 2013

(86) PCT No.: PCT/IB2013/054104
§ 371 (c)(1),
(2) Date: Nov. 20, 2014

(87) PCT Pub. No.: WO2013/175379
PCT Pub. Date: Nov. 28, 2013

(65) Prior Publication Data
US 2015/0155068 A1    Jun. 4, 2015

Related U.S. Application Data

(60) Provisional application No. 62/650,519, filed on May 23, 2012.

(51) Int. Cl.
| | | |
|---|---|---|
| *H01B 1/12* | (2006.01) | |
| *C12P 19/02* | (2006.01) | |
| *B01J 13/08* | (2006.01) | |
| *F28D 20/02* | (2006.01) | |

(52) U.S. Cl.
CPC .............. *H01B 1/12* (2013.01); *B01J 13/08* (2013.01); *C12P 19/02* (2013.01); *F28D 20/023* (2013.01); *Y02E 60/145* (2013.01)

(58) Field of Classification Search
None
See application file for complete search history.

(56) References Cited

U.S. PATENT DOCUMENTS

| | | | | |
|---|---|---|---|---|
| 6,808,557 | B2* | 10/2004 | Holbrey | A01N 25/10 106/163.01 |
| 2004/0038031 | A1* | 2/2004 | Holbrey | A01N 25/10 428/402.24 |
| 2009/0211720 | A1 | 8/2009 | Myllymaki | |
| 2011/0180751 | A1* | 7/2011 | Rein | C08B 1/003 252/182.12 |
| 2011/0190402 | A1 | 8/2011 | Linhardt | |

FOREIGN PATENT DOCUMENTS

| | | |
|---|---|---|
| EP | 2354165 A1 | 8/2011 |
| WO | 2005105278 A2 | 11/2005 |

OTHER PUBLICATIONS

Min Hoo Kim et al: "Entrapment of enzymes into cellulosebiopolymer composite hydrogel beads using biocompatible ionic liquid", Journal of molecular Catalysis. B, Enzymatic, Elsevier, Amsterdam, NL, vol. 75, Nov. 12, 2011, pp. 68-72.
Rein DM et al: "Cellulose as a novel amphiphilic coating for oil-in-water and water-in-oil dispersions", Journal of Colloid and Interface Science, vol. 386, Issue 1, Nov. 15, 2012, pp. 456-463.
E. Webster: "Cavitation", Ultrasonics, vol. 1, Issue 1, Jan.-Mar. 1963, pp. 39-48.
P. Claes et al: "Maximum de conductivite des solutions aqueuses d'electrolytes", Electrochimica Acta, vol. 28, Issue 4, Apr. 1983, pp. 421-427.
J. Vila et al: "Great increase of the electrical conductivity of ionic liquids in aqueous solutions", Fluid Phase Equilibria, vol. 247, Issues 1-2, Sep. 15, 2006, pp. 32-39.
R. Avolio et al: "A multitechnique approach to assess the effect of ball milling on cellulose", Carbohydrate Polymers, vol. 87, Issue 1, Jan. 4, 2012, pp. 265-273.

* cited by examiner

*Primary Examiner* — Ralph Gitomer
(74) *Attorney, Agent, or Firm* — Roach Brown McCarthy & Gruber, P.C.; Kevin D. McCarthy

(57) ABSTRACT

The present invention provides a composition having an interior hydrophobic space encapsulated by at least one non-derivatized cellulose molecular layer surrounded by a hydrophilic medium. The invention also provides methods for making an oil-in-water dispersion or water-in-oil dispersion by mixing a hydrophilic medium, a hydrophobic composition and non-derivatized cellulose solution in an ionic liquid or pure non-derivatized cellulose hydrogel.

12 Claims, 14 Drawing Sheets

a
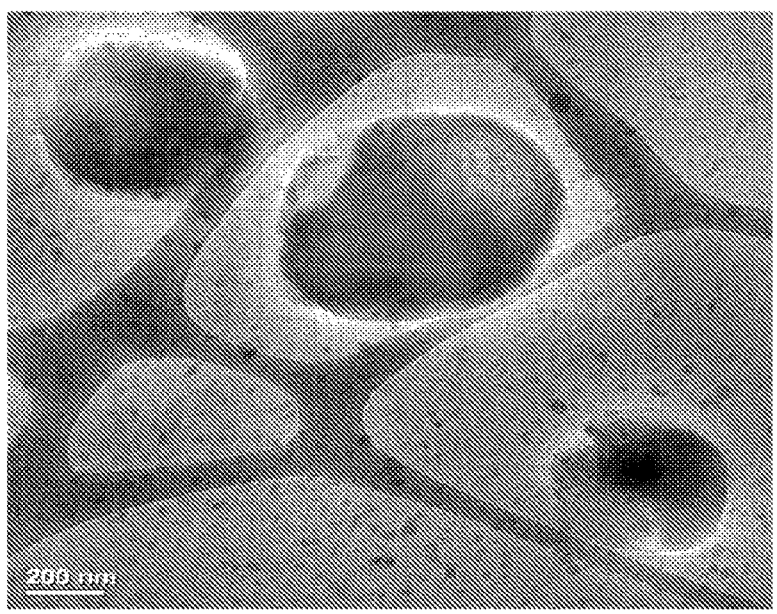
b
Figure 7 (A and B)

b a b

CELLULOSE CAPSULES

FIELD OF INVENTION

A composition having an interior hydrophobic space encapsulated by at least one non-derivatized cellulose molecular layer surrounded by a hydrophilic medium and methods for hydrolyzing cellulose and making an oil-in-water dispersion or water-in-oil dispersion, are provided.

BACKGROUND OF THE INVENTION

Encapsulation is a process in which tiny particles or droplets are surrounded by a coating to impart many useful properties to small capsules. In a relatively simplistic form, a microcapsule is a small sphere with a uniform wall around it. The material inside the microcapsule is referred to as the core, internal phase, or fill, whereas the wall is sometimes called a shell, coating, or membrane. Most microcapsules have diameters between a few microns to a few millimeters. The core may be a crystal, a jagged adsorbent particle, an emulsion, a suspension of solids, or a suspension of smaller microcapsules. The microcapsule even may have multiple walls. The reasons for microencapsulation are countless. In some cases, the core must be isolated from its surroundings, as in isolating vitamins from the deteriorating effects of oxygen, retarding evaporation of a volatile core, improving the handling properties of a sticky material, or isolating a reactive core from chemical attack. In other cases, the objective is not to isolate the core completely but to control the rate at which it leaves the microcapsule, as in the controlled release of drugs or pesticides. The problem may be as simple as masking the taste or odor of the core, or as complex as increasing the selectivity of an adsorption or extraction process.

The technique of microencapsulation depends on the physical and chemical properties of the material to be encapsulated: complex coacervation, centrifugal extrusion, vibrational nozzle, spray-drying, interfacial polycondensation, interfacial cross-linking, in-situ polymerization, etc.

The efforts towards thermal energy storage (TES) and sustainable energy technologies have been intensified over the past decades. Phase change materials (PCMs) can be directly used or consumed as a component of the composite-like energy storage materials (ESM) in TES applications like solar energy utilization, energy conserving in buildings, thermal insulation, thermal adaptable textile materials, etc. because they allow large amounts of heat to be stored during their melting and to be released during their solidifying process. A phase-change material is a substance with a high heat of fusion which, melting and solidifying at a certain temperature, is capable of storing and releasing large amounts of energy. Heat is absorbed or released when the material changes from solid to liquid and vice versa; thus, PCMs are classified as latent heat storage (LHS) units. Micron size dispersion of PCMs in the form of microparticles, microcapsules or PCM impregnated into open-cell foam-like supporting material make them more usable than the traditional block PCM because of: (i) protecting the PCM against the influences of the outside environment, (ii) increasing the heat-transfer area, (iii) permitting the core PSM to withstand changes in volume, as the phase change occurs and allowing small and portable TES system.

Many types of PCMs such as salt hydrates, paraffins, and fatty acids have been investigated. Among the studied PCMs, paraffins (alkanes) have been often used as a latent heat energy storage material (LHESM) with the advantages of high enthalpy of phase change, small segregation of components, small changes in structure and volume during repeated phase transitions (less than 10 v/v %), negligible super- and sub-cooling, low vapor pressure, self-nucleating behavior, very few safety constraints, high chemical stability, insolubility in water, biocompatibility, good recyclability and low cost. They have attractive thermal properties for different applications such as thermal adaptable fibers, thermal insulation building materials, heat exchangers in air conditioning and water heating systems.

The supporting material in the composite-like ESM is often made of high-density polyethylene or polypropylene, polyacrylamide, ceramics, silica powder or wood fiber-boards, poly(methyl methacrylate), poly(ethylene oxide), poly(ethylene terephthalate), silk fibroin-chitosan.

Since PCMs transform between solid to liquid and vice versa in thermal cycling, encapsulation naturally become the obvious storage choice. Other than the form stability and leakage resistance microencapsulated bulk PCMs promise additional advantages: (i) no need for additional storage container, thus reducing the cost of TES systems; (ii) minimizing the thermal resistance caused by PCM storage container; (iii) easily fabricated in desired shapes and dimensions; (iv) possibility to cut the ECM into arbitrary shapes without leakage. Most of the above ESM composites are prepared by immersing of the micronized PCM into supporting material by its direct incorporation at the mixing stage of material production.

Additional wide application field of PCMs is the fluid piping heat-transfer systems. In such conventional systems, thermal energy is transferred by the sensible heat of a single-phase working fluid, being proportional to the source/sink temperature difference. Because the systems are often operated with small temperature differences, the single-phase fluid must be pumped at a high-volume flow rate. As a result, the system consumes a large amount of pumping power. The use of PCM particles suspended in a single-phase working fluid (making so called slurry) provides additional thermal capacity from the latent heat associated with the solid/liquid phase change. This enhancement is due to a combination of four factors: (i) the often higher thermal conductivity of the added particles, (ii) the increased micro-convection due to the particles, (iii) a higher effective specific heat during the phase change process and, (iv) the greater temperature difference that is maintained as the phase change material melts/solidifies. The main merits of usage the microcapsulated PCM slurries are as follows: (i) the phase change temperature range could be well fitted for purposes of a specific system by properly selecting the PCM, (ii) the slurry particle size can be very small, which results in smaller frictional pressure loss for the same mass flow rate and less risk of clogging the transportation pipes, (iii) the extremely sharp viscosity decreasing in the bimodal diameter distribution dispersions, which sufficiently increases the pumping efficiency of the concentrated slurries.

It was found that nonencapsulated PCMs are sticky and can glue together to form large lumps; clogging often occurs in a piping system, resulting in failure to circulate the slurry through the system, so PCM encapsulation are recently widely used. The small (units of microns or less) PCM capsules were found a very stable during pumping, repeated circulations through a slurry flow circuit and multiply thermal cycling across the PCM melting temperature, therefore, this type of slurry can be treated as a conventional single-phase working fluid.

SUMMARY OF THE INVENTION

In one embodiment, the present invention provides a composition consisting or comprising an interior hydrophobic space encapsulated by at least one non-derivatized cellulose molecular layer, wherein the cellulose is surrounded by a hydrophilic medium In a further embodiment, the present invention provides a composition consisting or comprising an interior hydrophilic space encapsulated by non-derivatized cellulose molecular layer, wherein the cellulose is surrounded by a hydrophobic medium.

In a further embodiment, the present invention provides a composition consisting or comprising capsules in a hydrophilic medium, wherein the capsules having an interior hydrophobic space separated from the hydrophilic medium by at least one layer consisting non-derivatized cellulose.

In a further embodiment, the present invention provides a composition consisting or comprising capsules in a hydrophobic medium, wherein the capsules have an interior hydrophobic space separated from the hydrophobic medium by at least one layer consisting non-derivatized cellulose. In one embodiment, a composition as described herein is devoid of a surfactant. In one embodiment, a composition as described herein is oil-in-water composition. In one embodiment, a composition as described herein is water-in-oil composition.

In a further embodiment, the present invention provides a method for making an oil-in-water dispersion or water-in-oil dispersion, comprising the step of mixing a hydrophilic medium, a hydrophobic composition and non-derivatized cellulose solution in an ionic liquid.

In a further embodiment, the present invention provides a method for obtaining a solid-state, stable, dispersion of the composition as described herein by simply drying the composition.

DETAILED DESCRIPTION OF THE INVENTION

Figure 1:
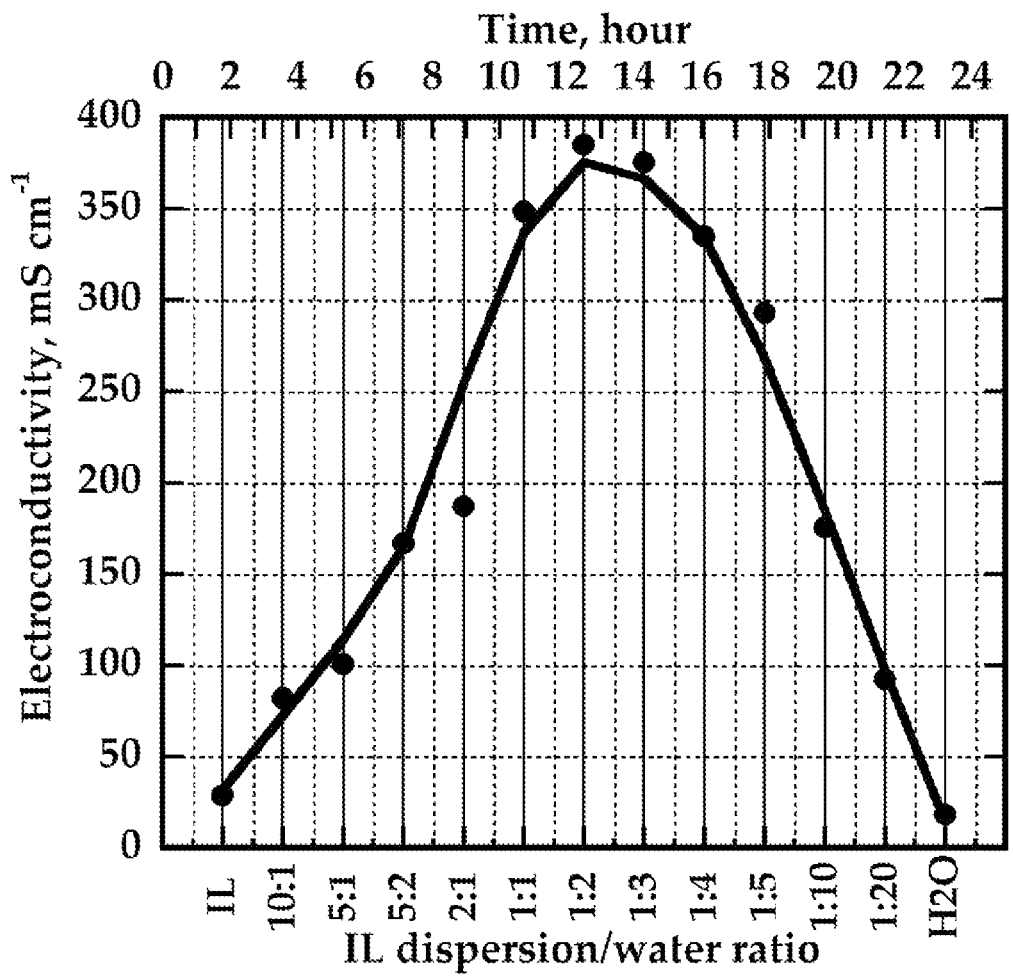
FIG. 1. A graph showing the electrical conductivity of dispersion as a function of the relative volumetric water content (IL means more than 95% vol. ionic liquid, H2O means less than 1% vol. of IL in solvent). The top axis indicates the time required to achieve the corresponding conductivity during dialysis against pure water.

The present invention provides the use of pure microcrystalline cellulose as an encapsulating agent. Pure microcrystalline encapsulates according to the invention hydrophobic or oily substances or compositions. The addition of pure microcrystalline cellulose to oil in water or water in oil compositions forms hydrophobic/oil core surrounded by a layer or layers of pure microcrystalline that are further surrounded by a hydrophilic solution such as an aqueous solution.

In another embodiment, provided herein a composition consisting or comprising an interior hydrophobic space encapsulated in non-derivatized cellulose, wherein the cellulose is surrounded by a hydrophilic medium and a method for making the same. In another embodiment, provided herein a composition consisting or comprising capsules in a hydrophilic medium, wherein the capsules have an interior hydrophobic space separated from the hydrophilic medium by at least one layer consisting non-derivatized cellulose. In another embodiment, provided herein a composition consisting or comprising capsules in a hydrophobic medium, wherein the capsules have an interior hydrophobic space separated from the hydrophobic medium by at least one layer consisting non-derivatized cellulose. In another embodiment, provided herein a composition consisting or comprising a pure non-derivatized cellulose hydrogel or hydrogel capsule.

In some embodiments, the composition described herein is devoid of a surfactant. In another embodiment, provided herein a composition consisting capsules in a hydrophilic medium, the capsules having an interior hydrophobic space separated from the hydrophilic medium by at least one layer consisting non-derivatized cellulose.

In another embodiment, cellulose in its unmodified form is utilized as a novel emulsifier for formation oil-in-water or water-in-oil dispersions based on encapsulation. In another embodiment, cellulose in its unmodified form is underivatized cellulose. In another embodiment, dried dispersions of hydrophobic compounds encapsulated by cellulose are readily regenerated by re-dissolution in water. In another embodiment, blowing of damp dispersions yields nanoporous cellulose foam (aerocellulose). In another embodiment, cellulose-encapsulated eicosane dispersions in solid or liquid form possess high effective heat-absorption capacity. In another embodiment, the encapsulating cellulose shell promotes the emergence of an irregular crystalline structure of the core material.

If the contact angle of water with a compound is less than 30°, the compound is designated hydrophilic since the forces of interaction between water and the compound's surface nearly equal the cohesive forces of bulk water, and water does not cleanly drain from the surface. If water spreads over a surface, and the contact angle at the spreading front edge of the water is less than 10°, the compound is often designated as superhydrophilic provided that the compound's surface is not absorbing the water, dissolving in the water or reacting with the water. On a hydrophobic surface, water forms distinct droplets.

As the hydrophobicity increases, the contact angle of the droplets with the surface increases. Compound's surfaces with contact angles greater than 90° are designated as hydrophobic. The theoretical maximum contact angle for water on a smooth surface is 120°. Microtextured or micropatterned surfaces with hydrophobic asperities can exhibit apparent contact angles exceeding 150° and are associated with superhydrophobicity and the so-called "lotus effect.

The term "hydrophilic", in some embodiments, refers to molecules that typically have polar groups. The term "hydrophobic", in some embodiments, refers to molecules that are typically free of polar groups. In some embodiments, the boundary between hydrophobicity and hydrophilicity occurs when the difference between the apolar attraction and the polar repulsion between molecules or particles of material immersed in water is equal to the cohesive polar attraction between the water molecules. Under these conditions, the interfacial free energy of interaction between particles of a material, immersed in water (ignoring electrostatic interactions), $\Delta G^{IF}$, is exactly zero. When the $\Delta G^{IF}$ is positive, the interaction of the material with water dominates and the surface of the material is hydrophilic; when $\Delta G^{IF}$ is negative, the polar cohesive attraction between the water molecules dominates and the material is hydrophobic. Thus, the sign of $\Delta G^{IF}$ defines the nature of the surface and the magnitude of $\Delta G^{IF}$ and is used, in some embodiments, as the natural quantitative measure of the surface hydrophobicity or hydrophilicity.

In another embodiment, an interior hydrophobic space is the core or the nucleus of a capsule of the invention which comprises a hydrophobic material such as but not limited to a hydrocarbon. In another embodiment, an interior hydrophobic space comprises the hydrophobic interacting groups of underivatized cellulose.

In another embodiment, underivatized cellulose of the invention comprises up to 40% impurities. In another embodiment, underivatized cellulose of the invention comprises up to 35% impurities. In another embodiment, underivatized cellulose of the invention comprises up to 30% impurities. In another embodiment, underivatized cellulose of the invention comprises up to 25% impurities. In another embodiment, underivatized cellulose of the invention comprises up to 20% impurities. In another embodiment, impurities are organic impurities. In another embodiment, impurities include: lignin, hemicellulose, etc.

In another embodiment, an interior hydrophilic space is the core or the nucleus of a capsule of the invention which comprises a hydrophilic material such as but not limited to an aqueous solution. In another embodiment, an interior hydrophilic space comprises the hydrophilic interacting groups of underivatized cellulose.

In another embodiment, a medium is the solution which surrounds a capsule of the invention. In another embodiment, a medium is the solution which interacts with the outer surface of a capsule of the invention.

Encapsulated ESMs are generally synthesized with melamine-formaldehyde, urea-formaldehyde or gelatin-formaldehyde as the shell materials. However, formaldehyde is harmful to the health, the remnant of which should be reduced to meet the limitation by the medical standards, in particular, when ESM intends to use for textile.

The present invention provides for the first time the non-derivatized cellulose hydrogel or solution were used as a novel eco-friendly emulsifying agents for producing stable oil-in-water or water-in-oil dispersions.

When the cellulose/IL solution or cellulose hydrogel were added to the agitated hydrocarbon dispersion in water (oil-in-water), or to water droplets dispersed in agitated hydrocarbon (water-in-oil), stable dispersions were, surprisingly, obtained without use of any additional surfactant. The control experiments, i.e. physical mixtures of cellulose/IL solution and water as well as hydrocarbons/IL dispersion and water, did not yield any stable dispersion but exhibited coagulated cellulose hydrogel in the first case or instantaneous phase separation in the second.

In some embodiments, an interior hydrophobic space consists or comprises alkanes. In some embodiments, alkanes are used as the core material of ESMs due to their stable chemical properties, suitable thermal properties and low cost. In some embodiments, cellulose in its ionic liquid solutions is precipitated at room temperature by addition of water, methanol, ethanol, acetone etc., forming, hydro-alco-, acetono- and other cellulose lyogels, respectively. It was surprising and unforeseeable for the skilled worker that previously described process, without the use of any surfactants, leads to instant spontaneous emergence of the suspension, consists of alkanes encapsulated into cellulose shell.

Unlike known microfluidic methods of the production of cellulose capsules, the present process does not require special equipment and the individual attention of maker to every elaborated capsule. The cellulose capsules can have different diameter (from tens of nanometers to millimeters) with small dispersion of dimensions and controllable shell thickness. The novel ESM suspension has an immanent relatively high electroconductivity, which opens new wide fields of its use.

The novel method for encapsulation of materials in cellulose shells gives the possibility to obtain the novel "green" materials in the numerous fields of applications. The suggested process demands the non-expensive, non-harmful, non-dangerous and easy recyclable and biodegradable intermediate materials.

The novel, highly stable nano/micro-scale slurries, based on cellulose encapsulated PCMs, have a relatively low viscosity at high concentrations, which increases their pumping efficiency and permits to increase the slurry concentration up to 45 wt. %, that allows to enlarge the efficiency of thermal energy transfer systems. Producing the slurries with bimodal particle size distribution also allows sufficient decreasing the slurry viscosity. The novel solid ESMs have the ability to maintain the shape and mechanical properties (form stability) and have no any leakage of melted PCM during phase change process.

The novel cellulose shells have high elastic strength, excellent water and good fire resistance and very low chemical reactivity. The novel IL based electroconductive PCM slurry makes it possible to use it in electrical induction heating loops and could be easily pumped using of magnetohydrodynamic pumps in the compact thermal exchange systems.

Moreover, common microencapsulated phase change materials have several inherent problems, such as low thermal conductivity, big volume change of the core PCM, the thermal and mechanical instability at pumping and high viscosity of concentrated slurry compositions, decreasing their pumping efficiency.

The main shortcomings of the existing bulk ESM are low ability to maintain the shape and mechanical properties (form stability) and the leakage of melted PCM during phase change process, which may be a problem over a long period of material exploitation. These effects limit the possible amount of PCM in the ESM (usually up to 10-30 w/w %), that, in turn, reduces the efficiency of thermal energy transfer system.

Some ESMs tend to solidify at the edges of the containers preventing effective heat transfer. The common problems of the known shell materials have a scarce sealing tightness, endurance, elastic strength, water and fire resistance and high chemical reactivity. Much effort is still needed to improve the performance ESM, such as specific heat, thermal conductivity and durability, and to understand the flow and heat transfer characteristics of slurries from encapsulated PCMs, so as to promote the applicability at the industrial scale.

The novel use of non-derivatized microcrystalline cellulose seems a very promising material for use as a shell in microcapsulated ESMs both solid and fluidized, because of its excellent physical and chemical properties and biocompatibility, but up to now does not used in these applications because of great difficulties in microcrystalline cellulose dissolution in the conventional solvents.

According to the invention cellulose/IL solution or cellulose hydrogel were added to an agitated hydrocarbon dispersion in water (oil-in-water), or to water droplets dispersed in agitated hydrocarbon (water-in-oil), and stable dispersions were obtained without use of any additional surfactant. Therefore the invention includes a composition consisting water (oil-in-water), or water droplets dispersed in agitated hydrocarbon (water-in-oil) and non-derivatized cellulose/IL solution or non-derivatized cellulose hydrogel. Surprisingly, the invention provides that the composition is free of a surfactant. Non-derivatized cellulose of the invention is, in some embodiments, in a crystal form.

Thus cellulose plays the role of a novel eco-friendly emulsifying agent. Surprisingly, for the duration of about a year neither reversible (flocculation) nor irreversible (coalescence) changes of dispersions have been observed.

The solid-state dispersion, obtained by drying liquid dispersions of non-volatile compounds such as paraffin oil or eicosane, can be repeatedly dissolved in excess water to re-form a sustainable dispersion. Complete re-dispersion occurs in less than a minute under common agitation or sonication. The re-dispersion effect is not observed with more volatile compounds such as heptane, which are lost during drying. This effect may be useful in application as self-emulsifying drug delivery systems. Attempts to extract the hydrocarbon within the solid-state dispersion using polar organic solvents (ethyl ether, dichloromethane) have failed, indicating the integrity of a continuous cellulose barrier on the encapsulated hydrocarbon.

The invention provides, novel methods for encapsulation materials in non-derivatized cellulose shell which permits the fabrication of vitamins isolated from the deteriorating effects of oxygen, retarding evaporation of a volatile core, improving the handling properties of a sticky material, isolating a reactive core from chemical attack, controlled release of drugs or pesticides, masking the taste or odor of the core or increasing the selectivity of chromatography or adsorption/extraction processes. The invention provides, the use of the present compositions which include a non-derivatized cellulose shell/capsule in: adhesives, carbonless copy papers, e-papers or e-inks, scratch-n-sniffs, self-healing materials, environment adaptive textiles, visual indicators, etc.

The novel phase change materials, fabricated according to the present invention, can be directly used or consumed as a component of the composite-like energy storage materials in thermal energy storage and sustainable energy technologies and applications like solar energy utilization, energy conserving in buildings, thermal insulation, thermal adaptable textile materials, autonomous heat exchangers for the electric power transformers, etc.

In some embodiments, solid ESMs are used as heat storage media for electrical boiler to peak shift of electrical demands by storing heat at night and releasing the heat in the daytime. Furthermore, there is much waste heat discharged from flue gas and water vapor at the phase change temperature zone in industry. ESMs can absorb this heat for temporary storage and can dissipate this heat for later use in its common phase change temperature range of 40-90° C.

Encapsulated ESM can be readily dispersed into carrier fluids to form liquid ESM slurries, which can be used as both the heat transfer and energy storage media, in particular for the secondary refrigeration or air conditioning loop systems.

The system with PCM can reduce the volume of the heat storage tanks compared to the system with water for heat storage. As is known, the ESM slurry is mainly made of PCM and water. So, in the phase change temperature range of PCM, it not only store or release sensible heat with the help of water contained in the slurry, but also latent heat with the help of PCM contained in the ESM. Under the condition of storing the same amount of heat, the system with ESM can sufficiently reduce the volume of the heat storage tanks.

The system with PCM can reduce pumping power consumption compared to water as heat transfer media due to latent heat. Compared to water for heat storage and transfer media, the PCM has larger heat storage density and can reduce pumping power consumption in transportation.

Because of relatively high electroconductivity, the present novel ESM slurry is ready for use in electrical induction heating loops and could be easily pumped by use of magnetohydrodynamic pumps in compact thermal exchange systems, which are extremely economic, portable and reliable because of the absence of electric heating spirals and any solid rotation and friction parts, in particular in in a closed-circuit portable heat exchange systems for automobile, airplane or rocket engines.

If oil and water are mixed and small oil droplets are formed and dispersed throughout the water, eventually the droplets will coalesce to decrease the amount of energy in the system. However, if small (100-1000 nm) solid particles in form of powder are added to the mixture, they will bind to the surface of the interface and prevent the droplets from coalescing thus causing the emulsion to be more stable. In the generalized form, in the two-phase system, consisting of two immiscible liquids, the small solid particles can behave like molecules of surface active substances—surfactants (typical molecular size<1 nm). This type of emulsion was named after S. U. Pickering.

In some embodiments, properties such as hydrophobicity, shape, and size of the particle have an effect on the stability of the emulsion. As provided hereinabove, the particle's contact angle to the surface of the droplet is a characteristic of the hydrophobicity. If the contact angle of the particle to the interface is low, the particle will be mostly wetted by the droplet and therefore will not be likely to prevent coalescence of the droplets. Particles that are partially hydrophobic (i.e. contact angle of approximately 90°) are better stabilizers because they are partially wettable by both liquids and therefore bind better to the surface of the droplets. Generally the phase that preferentially wets the particle will be the continuous phase in the emulsion system.

In some embodiments, adsorbing particles on the borders of droplets is not reversible. The difference in the behavior of particles and surfactants is due to the fact that molecules of surfactants have a separated in space hydrophilic and hydrophobic parts, whereas the Pickering particles have an isotropic surface. Therefore, small solid particles cannot be packed in structures like micelles and they cannot be amphiphilic. In some embodiments, a disadvantage of Pickering emulsions is that they are susceptible to Ostwald ripening, whereby diffusion through the continuous phase and between the droplets of the disperse phase (because of gaps between Pickering particles) can lead to an increase in the median droplet diameter over time or evaporation of the droplet content. This increase in droplet diameter increases the rate of separation of the disperse phase driven by density differences—either sedimentation or cream formation due to buoyancy. Ultimately this ripening can render the product unfit for use because for example it requires re-homogenization, or because the droplets are too coarse to remain dispersed in the spray tank prior to application to the target, or because the droplets are too large to give even distribution of the active ingredient when applied to the target.

In some embodiments, non-derivatized microcrystalline or microfibrillar crystal cellulose powder of the invention, being partially wetted by both aqueous and oil phases, may adsorb at aqueous-oil interfaces and is capable of stabilizing emulsions (Pickering effect). A densely packed monolayer of cellulose particles or a three-dimensional network of particles of the present invention provides unexpected stability of these emulsions.

The cellulose particles remain at all time, in some embodiments, in an initial microcrystal or fibrillar crystal form (before and after formation of dispersions). This particles form interrupted mechanical scaffolding barrier around dispersed material, which does not hermetically covers of the droplets. In one embodiment, this hermetic molecular cellulose shell hinders the growth of the median droplet diameter over time and/or evaporation of the volatile droplet content.

In some embodiments, the compositions of the invention comprise a covering material that comprises or consists a non-particulate and non-crystal material—the cellulose of the invention. In some embodiments, the compositions of the invention are characterized by enveloping of droplets by continuous non-derivatized cellulose molecular layer(s) (at least one layer) or cellulose molecular network, which hermetically covers of the droplets.

In another embodiment, drying of the compositions of the invention allows obtaining the reversibly dissolvable solid-state dispersions. In another embodiment, drying is drying at least 90% of the water or liquid content. In another embodiment, drying is drying at least 95% of the water or liquid content. In another embodiment, drying is drying at least 98% of the water or liquid content. In another embodiment, drying is drying at least 99% of the water or liquid content.

In another embodiment, cellulose hydrogel capsules of the invention are suspended in an aqueous liquid and used as surprisingly efficient medium for the enzymatic hydrolysis of cellulose to glucose. In another embodiment, provided herein a method for high-efficiency hydrolysis of cellulose to glucose. In another embodiment, provided herein a method for high-efficiency production of bio-fuel (ethanol) by subsequent fermentation. In another embodiment, provided herein a method for increasing cellulose enzymatic accessibility. In another embodiment, provided herein a method for overcoming cellulose hydrolysis recalcitrance.

In another embodiment, cellulose hydrogel capsules of the invention suspended in an aqueous media, and comprising a cellulose hydrolyzing enzyme, provides enhancement of cellulose hydrolysis into glucose. In another embodiment, this efficiency is achieved due to a unique combination of five factors: (i) exceptionally high hydration of the cellulose hydrogel shell (liquid/cellulose weight ratio up to 99:1), (ii) full absence of crystallinity in cellulose hydrogel shell, (iii) exceedingly small cellulose shell thickness (less than 100 nm), (iv) high cellulose hydrogel porosity (about 3 cm/g) and (v) very high cellulose hydrogel shell specific surface area (more than 600 $m^2$/g).

In another embodiment, cellulose hydrogel capsules comprising a cellulose hydrolysis enzyme is provided in a phase-change material (PCM) as the oil embedded in the capsule (see Rein D M, Khalfin R and Cohen Y, J. Coll. Inter. Sci. 386, 456 (2012) which is hereby incorporated by reference in its entirety). In another embodiment, the PCM system further promotes a beneficial spatial arrangement of the cellulose molecular planes in the hydrogel shell that further enhance the hydrolyzing enzymatic activity.

In another embodiment, the phase change of the PCM oil within the cellulose coated capsules from liquid to crystalline phase, in the cooling stage of the dispersion process, provides and added beneficial effect: the process of crystallization is accompanied by a reduction of the PCM core volume, thus the gap, formed between the cellulose hydrogel shell and the crystalline PCM core, is filled by the surrounding liquid with the enzyme that penetrates into the particle gap through the porous shell. In another embodiment, the phase change of the PCM oil within the cellulose coated capsules allows additional increase of the enzymatic hydrolysis caused by the optimal orientation of cellulose molecules turned to the internal side of the PCM particle shell. In another embodiment, the phase change temperature range of the PCM core material is specifically adjusted for optimum hydrolysis process.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

The cellulose shell encapsulation method represents a kind of coacervation process and consists from the several stages:

Cellulose Solution and Hydrogel Preparation

Initial solution was prepared by dissolution of different amounts of cellulose microcrystalline powder (3-15 wt. %) in the EMIMAc, pre-heated in the water bath to about 85° C. A magnetic stirrer was applied to the solution up to full cellulose dissolution during less than 10 min. It was found that practically instantaneous uniform dissolution can be achieved by impregnating the cellulose batch with the small amount of a highly volatile diluent (for example, dichloromethane). To limit cellulose decomposition due to the high exothermic effect accompanying the dissolution process, the solution temperature should not exceed 120° C. Cellulose hydrogel was prepared by immersing the solution under mild stirring in a water coagulation bath at room temperature for about 5 min. The regenerated cellulose hydrogel was washed thoroughly with deionized water.

Prior to cellulose dissolution in the ionic liquid, the crystalline powder was impregnated with a small amount of volatile liquid. Several liquids were evaluated: acetone, chloroform, diethyl ether, acetonitrile, and pyridine. Results were approximately the same, and thus we chose dichloromethane ($T_{boil}$=40° C.), which can be evaporated from the reaction zone fully and rapidly, without "explosive boiling" in the context of our experiments.

Preparation of Hydrocarbon Dispersion in Cellulose Solution

Features of ultrasonic emulsification: the process of ultrasonic emulsification commences when a certain intensity of irradiation is attained, this intensity being the cavitation threshold. The rate of emulsification increases with increasing irradiation intensity and decreasing liquid viscosity. For any intensity, there is a corresponding maximum concentration of emulsion that can be produced; this limiting concentration increases with increasing intensity. Its existence is ascribed to the attainment of an equilibrium state between the two conflicting processes of emulsification and coagulation. An increase in temperature reduces the emulsification efficiency because of an increasing trend toward coagulation. The size of the particles constituting the dispersed phase is dependent on the acoustic intensity and the time of irradiation. [E. Webster, *Ultrasonics* 1 (1963) 39]. In the preliminary experiments it was found that to effectively overcome the cavitation threshold in our experimental conditions, it was necessary to expose the investigated solutions of 20 or 50 mL to sonic power of about 130 or 310 W, respectively, for a duration of about 10 min at temperature of about 110° C. Easier and more uniform ultrasonic cavitation promotes by existence of gaseous traces of dichloromethane in the mixture.

A batch of hydrocarbon, either as crushed solid, melt or solution in DCM, was introduced directly into the heated cellulose/IL solution. The obtained mixture was subjected to the ultrasonic emulsification by the tip sonicator. At elevated viscosities, when the cellulose concentrations exceeds 10 wt. %, small amounts of diluent (1 wt. %), such as acetonitrile or pyridine, was added to the solution to reduce its viscosity. In order that the entire volume of processed liquid is involved in the ultrasonic cavitation, the sonicator's tip was continually moved across the boundary between the IL solution and the hydrocarbon up to complete disappearance of boundary.

Hydrocarbon Encapsulation in the Cellulose/IL Solution

Coacervation was induced by adding excess deionized water to the sonicated mixture (about 4:1 volume ratio). Water temperature could be either above or below the phase transition temperature of the core material (for eicosane the suitable range is 20-70° C.).

Preparation of Dispersions Using Cellulose Hydrogel

Cellulose hydrogel pieces were added at ambient conditions to the agitated hydrocarbon dispersion in water (oil-in-water), or to water droplets dispersed in agitated hydrocarbon (water-in-oil) with subsequent sonication for 10 min. About 4 g of hydrogel containing 5 wt. % of cellulose were added per 1 g of hydrocarbon or water, to obtain a stable oil-in-water or water-in-oil dispersion, respectively.

Thickening and Drying of the Obtained Liquid Dispersion

The hydrocarbon/cellulose dispersion in the IL/water solution was subjected to dialysis against pure water for 24 hours. This enabled exchange of EMIMAc with water in controlled manner (details provided in supplemental information). IL-free aqueous dispersions were thus obtained either as described above or by the direct use of the cellulose hydrogel as emulsifier. These were further dialyzed against 20 wt. % aqueous PEG solution at ambient temperature for 24 hours, followed by oven desiccation for 4 hours at 60° C. to yield a so-called "solid-state dispersion.

Electroconductivity of hydrocarbon/cellulose water/IL dispersions: in order to estimate the necessary duration of the dialysis process of the cellulose/IL solutions against pure water, different times and temperatures of dialysis were investigated. Variation of these parameters yields dispersions with different IL content in the water and, as a result, with different electrical conductivities. Experimental results are shown in FIG. 1, electroconductivity was measured with a Precision Impedance Analyzer Agilent 4294A (Agilent Technologies Co., USA) at 0.5 V and 10 kHz. It is observable that the electrical conductivity of a dispersion dramatically increases with water content up to a maximum at a ratio of water to cellulose/IL dispersion of 1:2, and then decreases. The increase in the electrical conductivity from the value of the pure IL based dispersion to the value at the maximum is about 13 times. A peak in the conductivity also appears for the majority of concentrated electrolyte solutions. [P. Claes, Y Loix, J. Glibert, *Electrochim. Acta*, 28 (1983) 421] This effect could be explained by the presence of two multidirectional mechanisms. One of them is the number of ions present to transport charge (which induces conductivity to increase with the IL concentration). The other one is related with the mobility of the ions in the solution, which will be lower when the number of ions increases (and so it induces conductivity to decrease with concentration). [J. Vila, P. Gines, E. Rilo, O. Cabeza, L. M. Varela, *Fluid Phase Equilibria* 247 (2006) 32] Data on changes of the electrical conductivity of dispersion in the dialysis permit estimation of the speed of dispersion dilution and confirms the nearly complete implementation of the dialysis process at room temperature through about of 24 hours.

Blowing of the Concentrated Precipitate

A different drying process of the IL-free aqueous dispersions was carried out in a rotary evaporator or vacuum oven (at about 35° C. and 0.67 kPa). In this case, blowing of concentrate occurred at the final stage of drying yielding a foam-like solid-state dispersion. As a core materials for encapsulation could be used a paraffins (alkanes) or fatty acids.

As an ionic liquid solvent for cellulose could be used 1-ethyl-3-methylimidazolium acetate (EMIMAc) or 1-butyl-3-methylimidazolium chloride, etc.

As a cellulose non-solvent could be used water, alcohols, ketones, chlorinated alkanes, etc.

N-Eicosane, with a purity of above 98% was supplied by Merk, Germany. Microcrystalline cellulose powder with particle size in range 20-160 μm and EMIMAc of 90% purity were supplied by Sigma-Aldrich Co. EMIMAc and cellulose were dried in a vacuum oven at 60° C. at 0.26 kPa for at least 24 hours. Polyethylene glycol (PEG, $M_w$= 20,000), light paraffin oil (mixture of saturated hydrocarbons with an average chain length of 11 carbon atoms), dichloromethane (DCM), ethyl ether, acetonitrile, pyridine and heptane were purchased from Sigma-Aldrich Chemicals. These chemicals were used without additional purification. Unless otherwise stated, the percentages of the components were calculated based on the total composition of the final mixture.

Equipment and Characterization Methods

Emulsification of the dispersions was performed using an Ultrasonic cell disrupter 2000U (Ultrasonic Power Corp., USA) equipped with finger-like tip. The morphology of the form-stable blends was investigated by a high resolution scanning electron microscope (HR-SEM) Ultra Plus Gemini (Zeiss Co., Germany) and cryogenic transmission electron microscope (cryo-TEM) $T12G^2$ (FEI Co., Netherlands). Vitrified samples for cryo-TEM were prepared in a controlled environment vitrification system (CEVS) at controlled temperatures (either 25 or 60° C.) and 100% relative humidity. A droplet of the dispersion was placed on the TEM grid covered by a holey carbon film and blotted from the back side to yield a thin liquid film spanning the holes. The sample was vitrified by plunging into supercooled liquid ethane. The specimen transfer to the microscope was done using an Oxford Instruments CT-3500 cryo-specimen cooling holder and transfer procedure. The samples were investigated using low dose electron imaging and acceleration voltage of 120 kV. Images were recorded using Gatan 791 MultiScan CCD camera and the image processing was done by Gatan Digital Micrograph 3.9.2 software package. A Mastersizer 2000 instrument (Malvern Co. Ltd., UK) was used to measure the particle size and distribution. Zeta-potentials of the dispersions were measured with a Zetasizer NanoZS instrument (Malvern Co. Ltd., UK), equipped with a He—Ne red light laser of 633 nm wavelength.

For the dialysis processes we used Spectra/Por® molecular porous membrane tubes (MWCO 12000-14000, volume/length=2 mL/cm, Spectrum Laboratories, Inc., USA).

The DSC measurements were realized on Mettler Toledo DSC 1 (Mettler-Toledo, Inc., USA) in temperature interval 5-100° C. at scanning rate: 10° C./min. TGA measurements were performed on TA Q5000-0486 Thermal Gravimetric Analyzer (TA Instruments Inc., USA), in temperature interval 20-370° C., at heating rate of 20° C./min.

X-ray diffractometry of the samples was performed on small/wide-angle diffractometer (Molecular Metrology SAXS system) equipped with a sealed microfocus tube (MicroMax-002+S) emitting Cu Kα radiation (λ=0.1542 nm).

EXAMPLES

Example 1: Preparation of Cellulose Solution

Initial solution was prepared by dissolution of cellulose microcrystalline powder (3-15 wt. %) in the preliminary heated EMIMAc (70-90° C.) using magnet stirrer during 10-20 min. For quicker and more uniform dissolution, the batch of cellulose could be preliminary "diluted" by the stirring in highly volatile diluent—dichloromethane in the weight ratio of 1 part of cellulose to 3 parts of liquid. It have been checked several liquids: acetone, chloroform, diethyl ether, acetonitrile, pyridine with the approximately same success, and, as a result, stopped our choice on dichloromethane, $T_{boil}$=40° C., which can be evaporate fully and rapidly, but without the "explosive boiling" in the context of our experiments.

Example 2: Preparation of Alkane Dispersion in Cellulose Solution

As a samples of alkanes were used heptane ($C_7H_{16}$), light paraffin oil and n-eicosane ($C_{20}H_{42}$).

First Variant.

The necessary batch of alkane could be introduced directly (in the solid or molten form) into the ready cellulose/IL solution or preliminary dissolved into aforesaid diluent liquid (if this is possible) before stirring with cellulose powder. As we use the dichloromethane, which is an excellent solvent for alkanes, we prepared the solutions of alkanes in weight ratio between alkanes and cellulose from 1:1 to 5:1. Prepared solution was poured into preliminary heated cellulose/IL solution. The obtained mixture was immediately subjected to the ultrasonic emulsification.

Second Variant.

Cellulose hydrogel pieces were added at ambient conditions to the agitated hydrocarbon dispersion in water. The obtained mixture was immediately subjected to the ultrasonic emulsification.

The process of ultrasonic emulsification commences when a certain intensity of irradiation is attained, this intensity being the cavitation threshold. The rate of emulsification increases with increasing intensity. For any intensity, there is a corresponding maximum concentration of emulsion that can be produced; this limiting concentration increases with increasing intensity. Its existence is ascribed to the attainment of an equilibrium state between the two conflicting processes of emulsification and coagulation. The frequency may also determine which of the two liquids becomes a disperse phase. Highly viscous liquids (more than about 0.2 Pa·s) do not readily emulsify due to big difference in the levels of the absorption of acoustic power one of liquids compared to other one, and an increase in temperature reduces the emulsification efficiency because of an increasing trend toward coagulation. Evidence of the dependence of ultrasonic emulsification is contained in the fact that it is impossible to emulsify degassed liquids: the emulsifying threshold decreases with increasing dissolved gases content. The size of the particles constituting the disperse phase is dependent on the acoustic intensity and the time of irradiation.

The initial properties of the 7.5 wt. % cellulose/IL solution heated to 50-90° C. was found acceptable for the efficient ultrasonic emulsification. In our experiments was found that for the 20 mL of the investigated liquid the optimum sonic power (determined by equilibrium between emulsification and coagulation processes) is about 130 W and for 50 mL is about 310 W during 5 min. Existence of gaseous traces of dichloromethane in the mixture promotes the ultrasonic cavitation. At lower temperatures the viscosity of solutions could be reduced by addition of small amounts of diluent, such as acetonitrile or pyridine.

Example 3: Coacervation of Joint Alkane/Cellulose Mixture

A complex coacervation of prepared joint alkane/cellulose mixture by its coagulation with excess of deionized water (about 20 mL of water per 20 mL of initial alkane/cellulose mixture was prepared; water temperature was 25-80° C.). As a result of complex coacervation process was obtained the milk-color suspension.

Obtained suspension was subjected to dialysis against pure water or 20 wt. % water solution of polyethylene glycol ($M_w$=20000) at room temperature during 8 hours and/or vacuum oven drying during 24 hours at 60° C.

Example 4: Properties of the Novel Cellulose Shell Encapsulated Thermal Energy Storage Materials As a result of the aforesaid procedures were obtained and investigated several samples of novel cellulose shell encapsulated thermal energy storage materials. In the samples, described below, the n-eicosane was used as a PCM material.

Sample 1.

Liquid suspension consists of 10 wt. % of cellulose encapsulated PSM in IL/water diluent (1:1 v/v), obtained according to method and procedure, discovered above.

Sample 2.

Liquid suspension consists of cellulose encapsulated PSM in pure water diluent after dialysis of initial suspension (as in sample 1) and following vacuum drying up to PCM/cellulose capsules content of 10, 20, 30 and 45 wt. %.

Sample 3.

Dry solid ESM, obtained after dialysis of initial suspension against pure water and vacuum drying of the material as in sample 2.

The below tables indicate the measured physical properties of the samples:

| Sample number | Particle concentration in diluent, wt. % | Heat of melting, J/g (vs. slurry concentration in water, wt. %) | | | | Heat of crystallization, J/g (vs. slurry concentration in water, wt. %) | | | |
|---|---|---|---|---|---|---|---|---|---|
| | | 10 | 20 | 30 | 45 | 10 | 20 | 30 | 45 |
| 1 | 10 | | 25 | | | | 29 | | |
| 2 | 10 20 30 45 | 25 | 45 | 75 | 101 | 27 | 48 | 77 | 105 |
| 3 | 100 | | 225 | | | | 229 | | |

| Sample number | Freezing temperature of slurry, ° C. | Subcooling and superheating of core, ° C. | Electrical conductivity of slurry, S/m | Encapsulation ratio, % | Average particle diameter, nm |
|---|---|---|---|---|---|
| 1 | −20 | <1 | 4.3 | 82 | 650 |
| 2 | ~0 | <2 | ~0.08 | 78 | 200 |
| 3 | — | <1 | — | 80 | ~300 |

| Sample number | Viscosity, mPa · s (vs. slurry concentration in water, wt. %) | | | | Viscosity of mixture (v/v) sample 1:sample 2 = 4:5 mPa · s |
|---|---|---|---|---|---|
| | 10 | 20 | 30 | 45 | |
| 1 | | 21.6 | | | 0.8 |
| 2 | 1.2 | 1.6 | 7.5 | 30.4 | |
| 3 | | — | | | — |

| Sample number | Thermal conductivity, W/(m · K) | Redilution by water | Melting temperature of core, ° C. | Accelerated thermal cycling test (3000 heat/cool cycles) |
|---|---|---|---|---|
| 1 | 0.5 | possible | ~37 | pass |
| 2 | ~0.6 | possible | 37-39 | pass |
| 3 | 0.25 | possible | ~37 | pass |

Formation of Cellulose Coated Oil-in-Water and Water-in-Oil Dispersions

Figure 5:
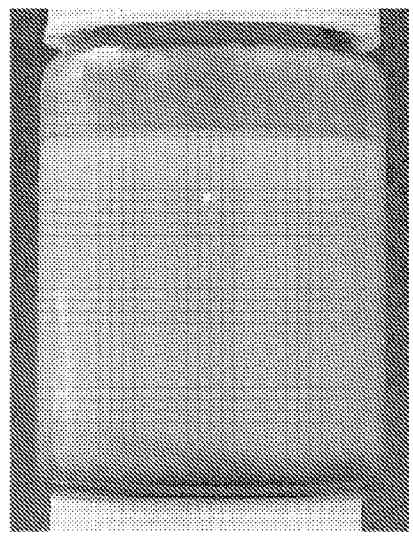
FIG. 5. A photograph showing the different eicosane/cellulose (4:1) dispersion samples: 6 wt. % microcapsulated water based dispersion (a); this dispersion dialyzed against 20 wt. % aqueous PEG solution for 24 hours followed by oven desiccation for 4 hours at 60° C. (sample mass 2.2 g) (b); dispersion concentrate, blown in vacuum oven at 60° C. (sample mass 0.4 g) (c).
Figure 5:
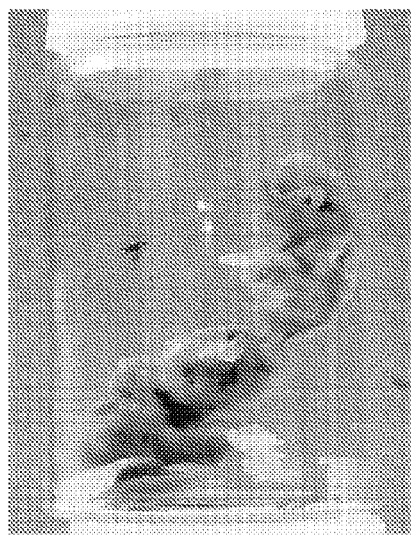
Figure 5:
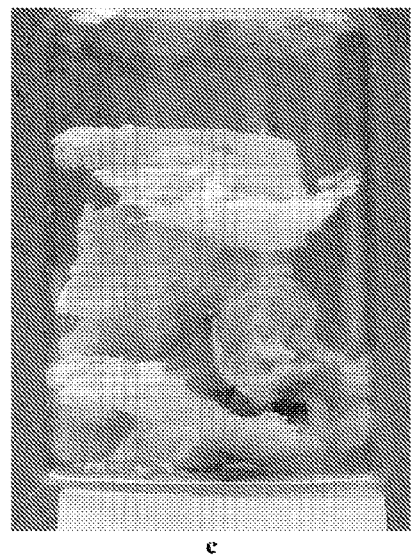

When the cellulose/IL solution or cellulose hydrogel were added to the agitated hydrocarbon dispersion in water (oil-in-water), or to water droplets dispersed in agitated hydrocarbon (water-in-oil), stable dispersions were obtained without use of any additional surfactant (FIG. 5a). The control experiments, i.e. physical mixtures of cellulose/IL solution and water as well as hydrocarbons/IL dispersion and water, did not yield any stable dispersion but exhibited coagulated cellulose hydrogel in the first case, or instantaneous phase separation in the second. We interpret the dispersion stability as due to the amphiphilic character of cellulose. This indicates that the macromolecules has been successfully exfoliated from their crystal structure, so as to present the hydrophilic hydroxyl groups to water, and the more hydrophobic planes of glucopyranose rings towards the hydrocarbon. Thus cellulose plays the role of a novel eco-friendly emulsifying agent. For the duration of about a year neither reversible (flocculation) nor irreversible (coalescence) changes of dispersions have been observed in the oil-in-water dispersions. Water-in-oil dispersions were somewhat less stable, and phase separation is observed after several months.

The solid-state dispersion, obtained by drying liquid dispersions of non-volatile compounds such as paraffin oil or eicosane, can be repeatedly dissolved in excess water to re-form a sustainable dispersion. Complete re-dispersion occurs in less than a minute under common agitation or sonication. The re-dispersion effect is not observed with more volatile compounds such as heptane, which are lost during drying. This effect may be useful in application as self-emulsifying drug delivery systems. Attempts to extract the hydrocarbon within the solid-state dispersion using polar organic solvents (ethyl ether, dichloromethane) have failed, indicating the integrity of a continuous cellulose barrier on the encapsulated hydrocarbon.

Figure 6:
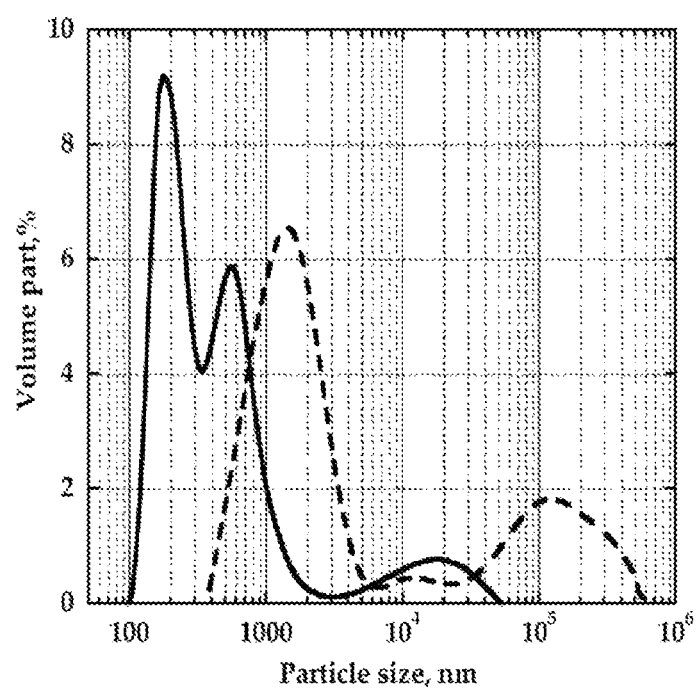
FIG. 6. Is a graph showing the particle size distribution of representative cellulose coated eicosane dispersion (eicosane/cellulose ratio 4:1) in water: native dispersion (solid line) and re-dissolved dispersion (dotted line).

The particle size distribution of the representative cellulose coated eicosane dispersion (eicosane/cellulose ratio 4:1) in water is shown in FIG. 6. It exhibits a trimodal distribution, peaked around 200, 550 and 20,000 nm. This may be due to non-optimized method of preparation, possibly resulting in non-uniform sonic energy distribution in the small vessel. No noticeable difference in the particle size distribution was observed after two weeks. The particle size distribution in the re-dissolved dispersion obtained by magnetic stirring with water differs from that of the original one, exhibiting larger particles size. Additional sonication reduces this difference.

Microcapsules Morphology

Figure 7C:
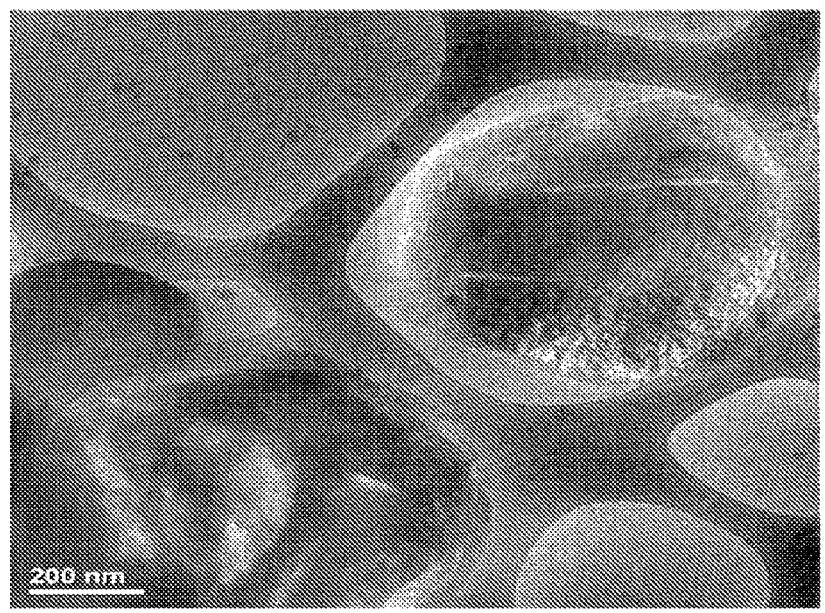
FIG. 7. Is a micrograph showing Cryo-TEM images of vitrified thin films of the aqueous dispersions: eicosane-containing particles vitrified before core crystallization (at 60° C.) (a), paraffin oil-containing particles vitrified at 20° C. (b), heptane-containing particles vitrified at 20° C.
Figure 8A:
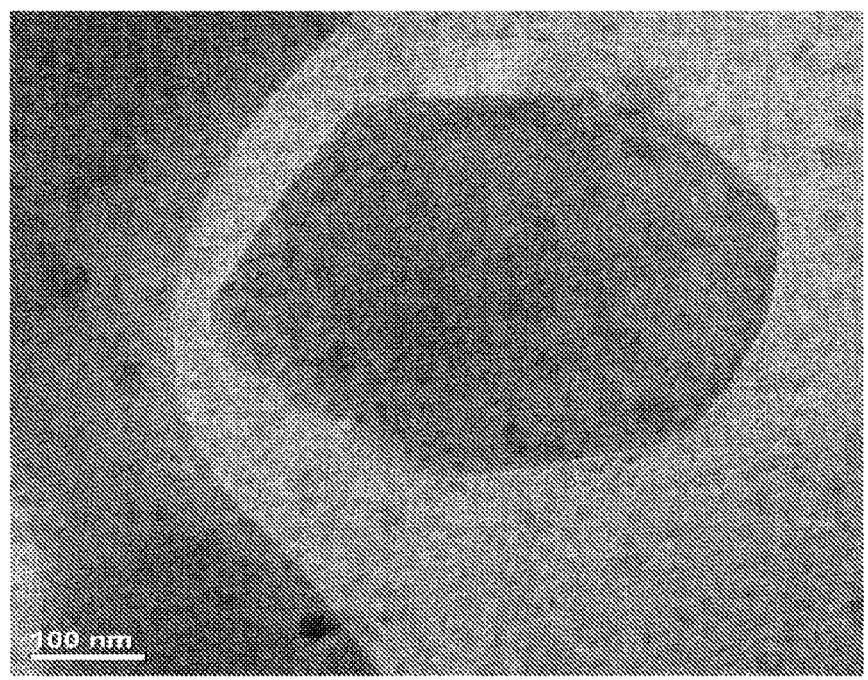
FIG. 8. Is a micrograph showing Cryo-TEM image of the aqueous eicosane-containing dispersion vitrified after core crystallization at ambient temperature. (a) image taken at low electron dose, (b) same area after electron irradiation at about 3000 e/nm2, arrow indicates the radiation stable shell.
Figure 8B:
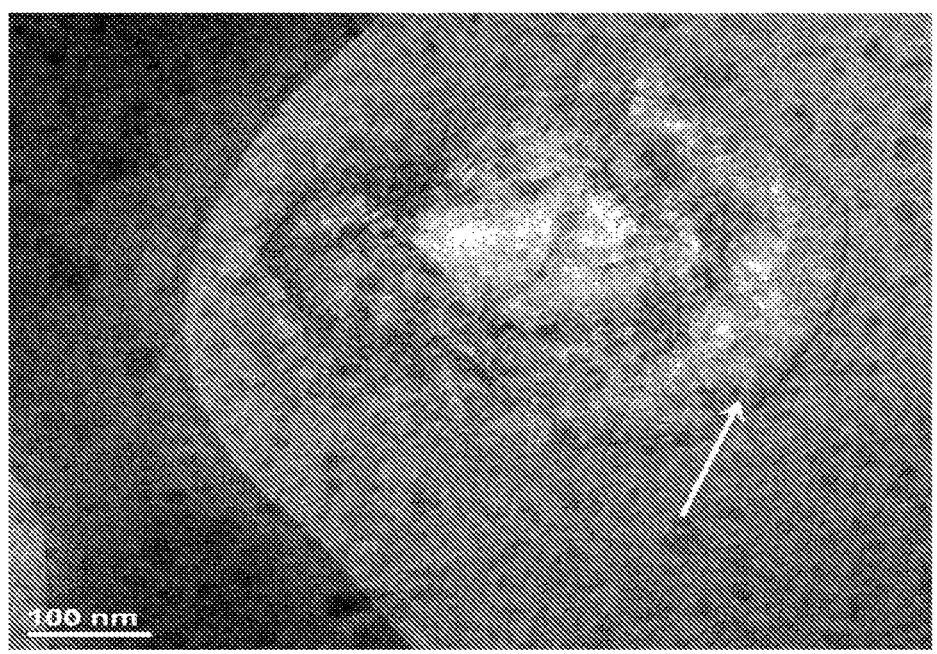

Cryo-TEM images of vitrified thin films of the aqueous dispersions are shown in FIGS. 7 and 8. The images show mostly isolated particles about 200 nm in diameter, as given by the main (first) peak of the particle size distribution. It should be noted that cryo-TEM imaging requires a thin film which prohibits observation of the larger particles. The particles mostly seem to have a uniform structure, with a rather smooth surface. Agglomerates of smaller particles are not observed, nor are small particles observed on the surface, as would be in the case of Pickering emulsions. The particles containing paraffin oil and heptane, exhibited a globular shape and a homogeneous surface (FIG. 7b,c). Eicosane-containing particles vitrified from 60° C., above its melting transition, exhibited a similar structure (FIG. 7a), whereas those vitrified after core crystallization (at ambient temperature) exhibit pronounced edges, following the contours of the crystal within them (FIG. 8), which exists in a triclinic crystal structure. The cryo-TEM image of the vitrified dispersions where taken at minimal electron dosage. When the sample is exposed to enhanced electron irradiation, as in FIG. 8b (3000 e/nm$^2$), noticeable radiation damage is observed in the dispersed oil. This is a well-known phenomenon due to water radiolysis forming radicals that degrade the hydrocarbons. Interestingly, a thin stable coating is observed and interpreted as the encapsulating cellulose shell, which may have significant water content (cellulose hydrogel).

Figure 9:
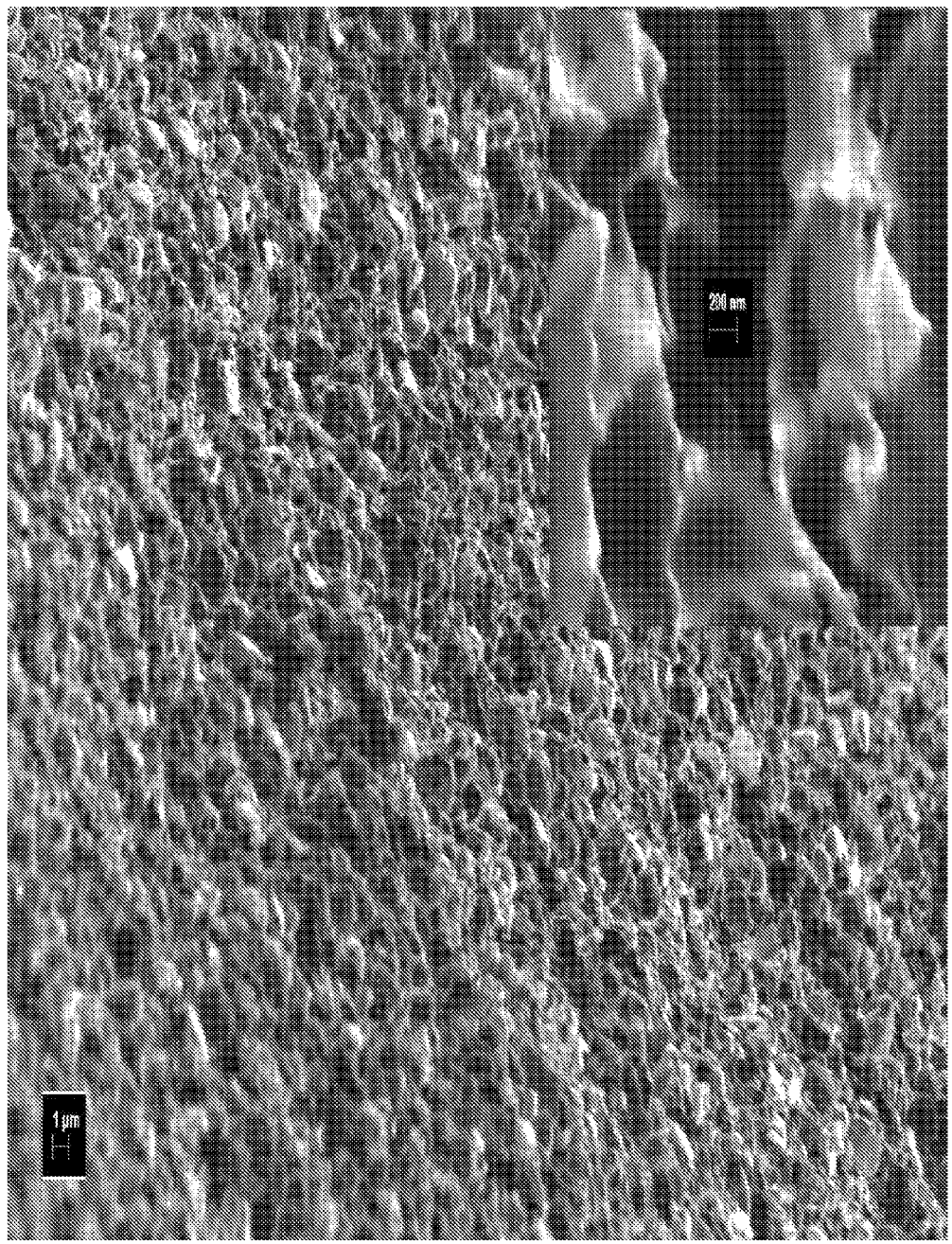
FIG. 9. Is a micrograph showing HR-SEM imaging of the cryo-fractured surface of the eicosane based sample. Inset: a higher magnification image of area where the fracture cut across the particles.
Figure 10:
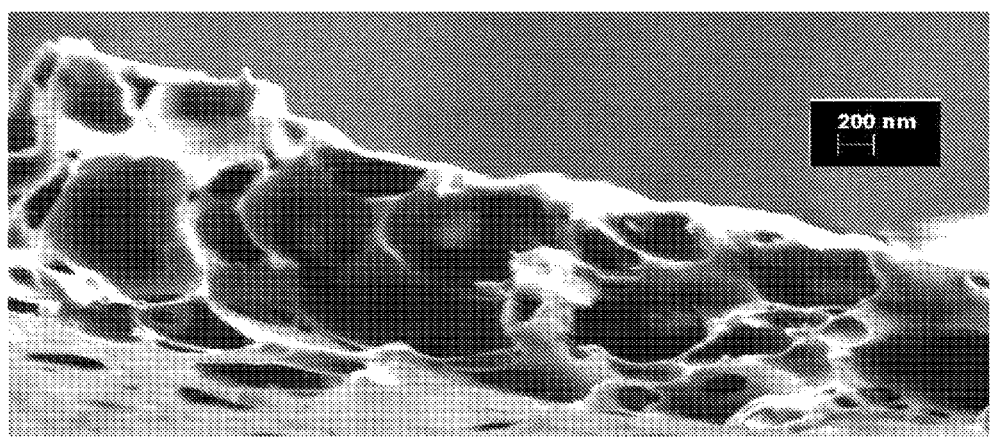
FIG. 10. Is a micrograph showing structures obtained after blowing of different dispersions: eicosane/cellulose (a); heptane/cellulose (b).
Figure 10:
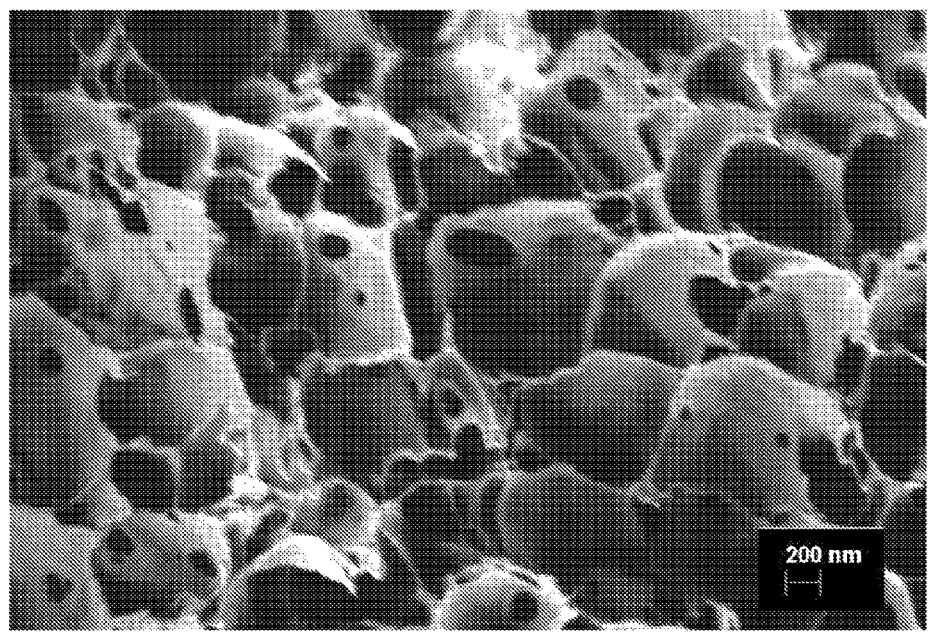

The morphology of the dried dispersions was investigated by HR-SEM imaging of the cryo-fractured surface. The fracture surface of the eicosane based sample is shown in FIG. 9. Microcapsules could be characterized by a smooth surface. They form a very condensed agglomerate structure without visible boundaries between the particles. The dispersed particles appear to be completely covered by the cellulose shell. In cases where the fracture cut across the particles (inset in FIG. 10), no trace of the encapsulated hydrocarbon could be observed in the broken capsules, which indicates poor adhesion between the core and its cellulosic shell. It also indicates that the cellulose shell thickness is less than 50 nm.

Morphology and Properties of the Blown Microcapsules

As mentioned above, drying the dispersion under reduced pressure can induce blowing at the final stage of drying yielding a nanoporous foam (aerocellulose). The blowing agent can be either the residual water, or the entrapped hydrocarbon if volatile. It is well known that non-derivatized cellulose hydrogel simply shrinks during drying and does not exhibit any blowing effects. The ease of the blowing process in the present case is related to the presence of the encapsulated hydrophobic material. Apparently it induced the formation of the cellulose hydrogel shell which encases it, possibly with some trapped water. The blowing of these capsules under reduced pressure at the last stage of drying results in the observed structures, as shown in FIG. 10a. A much more clearly defined cellular structure is observed when a volatile hydrocarbon is used, as shown for the case of heptane in FIG. 10b.

Z-Potential and Chemical (pH) Stability of Dispersion

Figure 11:
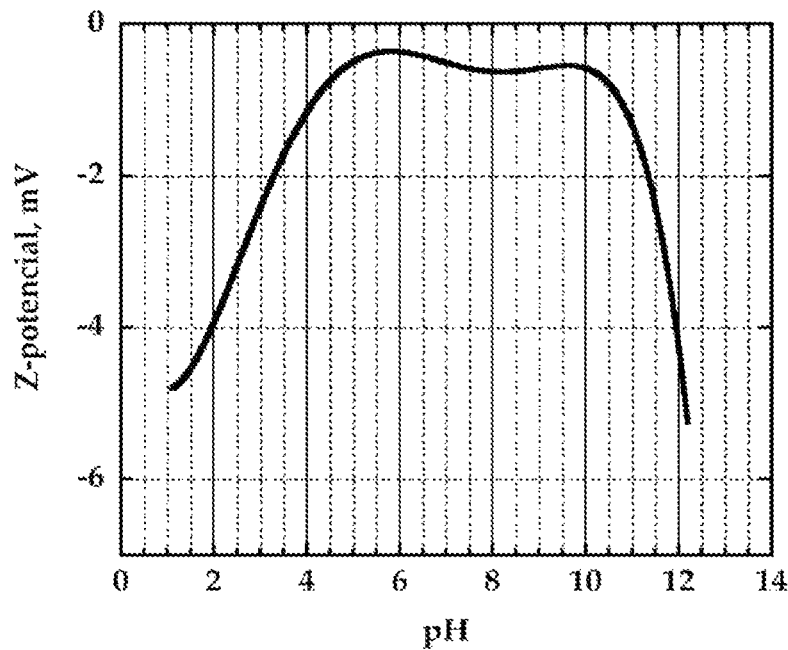
FIG. 11. Is a graph showing the pH dependence of the ζ-potential of cellulose coated eicosane dispersion.

FIG. 11 shows the pH dependence of the ζ-potential of cellulose coated eicosane dispersions. It very slow changes in the range of −1÷−5 mV, within the investigated pH interval of 2 to 13. This weak changing low value of the ζ-potential indicates that the particles are uncharged, thus the dispersion stability is not due to electrostatic repulsion. Therefore, one can conclude that the obtained very high stability of this dispersion is determined by the kinetic and hydration causes. For comparison, the ζ-potential of paraffin dispersions prepared with sodium dodecyl sulfate as surfactant, has significantly negative value (about −60 mV) in the same pH range.

Calorimetric Analysis of Solid and Liquid Eicosane/Cellulose Dispersions

Figure 12:
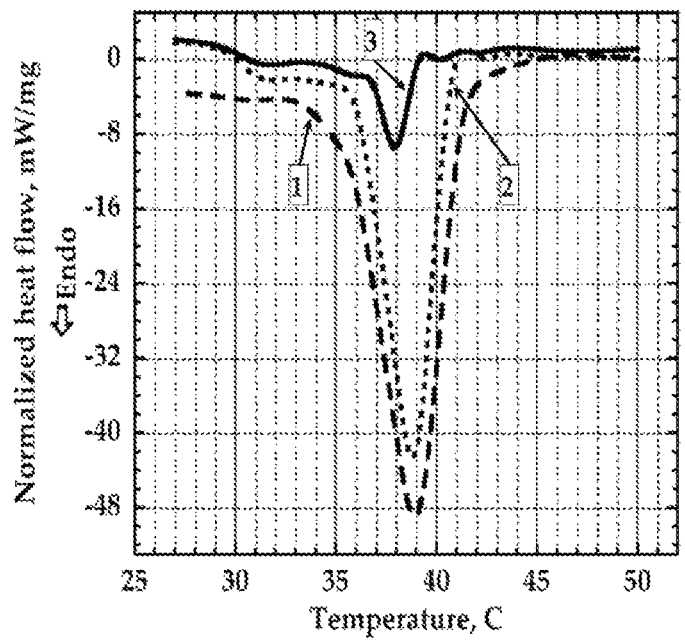
FIG. 12. Is a graph showing the Differential scanning calorimetry of pure eicosane (1), eicosane/cellulose (4:1) solid dispersion (2) and 6 wt. % aqueous suspension, re-dispersed from solid dispersion (3).
Figure 13:
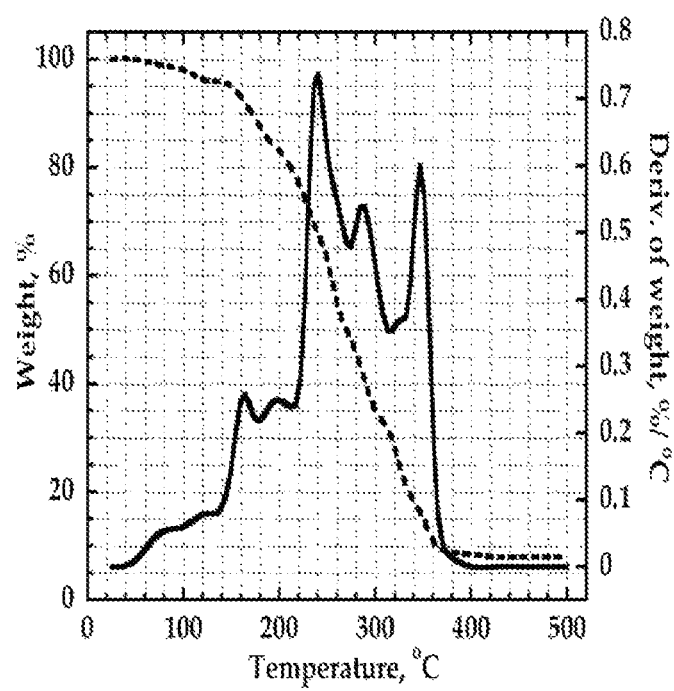
FIG. 13. Is a graph showing the TGA (dotted line) and DTG (solid line) of the solid eicosane/cellulose (4:1) microcapsules.

There is significant current interest in eicosane-based phase change materials for storage of thermal energy, due to its high latent heat, transitions temperature in a practical range of interest, and low cost. FIG. 12 presents results of differential scanning calorimetry (DSC) measurements on solid eicosane/cellulose (4:1) dispersions and 6 wt. % aqueous suspensions re-dispersed from them. The effective heat-absorption capacities of the solid dispersion and re-dispersed aqueous suspension are about 65% and 7% relative to pure eicosane, respectively. Thus, an effective heat-absorption capacity of even a 6% aqueous dispersion of eicosane in temperature range of 35-45° C. is 4 times greater than that of pure water. FIG. 13 shows the thermo-gravimetric analysis (TGA) and differential TGA (DTG) of the solid eicosane/cellulose (4:1) microcapsules. Initial DTG peaks between 50 and 160° C., corresponds to a mass loss of absorbed moisture of approximately 15%. The peaks in range of 180-320° C. (mass loss 70%) can be attributed to oxidation of the eicosane and degradation of the IL traces. The decomposition peak at about 350° C. can be attributed to decomposition and oxidative degradation of cellulose (mass loss 15%). These results indicate the good thermal stability of the eicosane/cellulose microcapsulated dispersion.

X-Ray Diffractometry

X-ray diffraction was used to investigate the crystalline features of the different components in the dried dispersions of eicosane/cellulose (4:1). The main features in the diffraction from the dried dispersion (line 3 in FIG. 14a) are due to the crystal packing of eicosane at ambient temperature, as shown in line 1 of FIG. 14a. This pattern is similar to that of pure eicosane crystallized from the melt, and does not exhibit the characteristic diffraction pattern of cellulose crystals (I or II types). Line 2 in FIG. 14a displays the diffraction from the same system heated to 60° C., above the melting temperature of eicosane. It displays a single broad maximum at about 20° which is due both to the amorphous halo of liquid eicosane and of amorphous cellulose (see supplementary material). Subtracting of the diffraction from the molten eicosane from that of the dried dispersion at the same temperature (60° C.) yields a residual halo very similar to that of amorphous cellulose obtained by milling the crystalline form, and is also similar to that obtained from the dried cellulose hydrogel obtained as described above, shown in line 4 of FIG. 14a. The insignificant cellulose crystallinity is in accord with the molecular-level arrangement of the cellulose macromolecules so that their hydrophilic parts turn to water and the hydrophobic parts towards the hydrophobic hydrocarbon. X-ray diffraction thus indicates that this amorphous state exists both in the regenerated cellulose hydrogel as well as in the cellulose-stabilized hydrocarbon dispersions, and is most likely due to the effect of the ionic liquid in unraveling the microfibrillar cellulose crystals.

Figure 2:
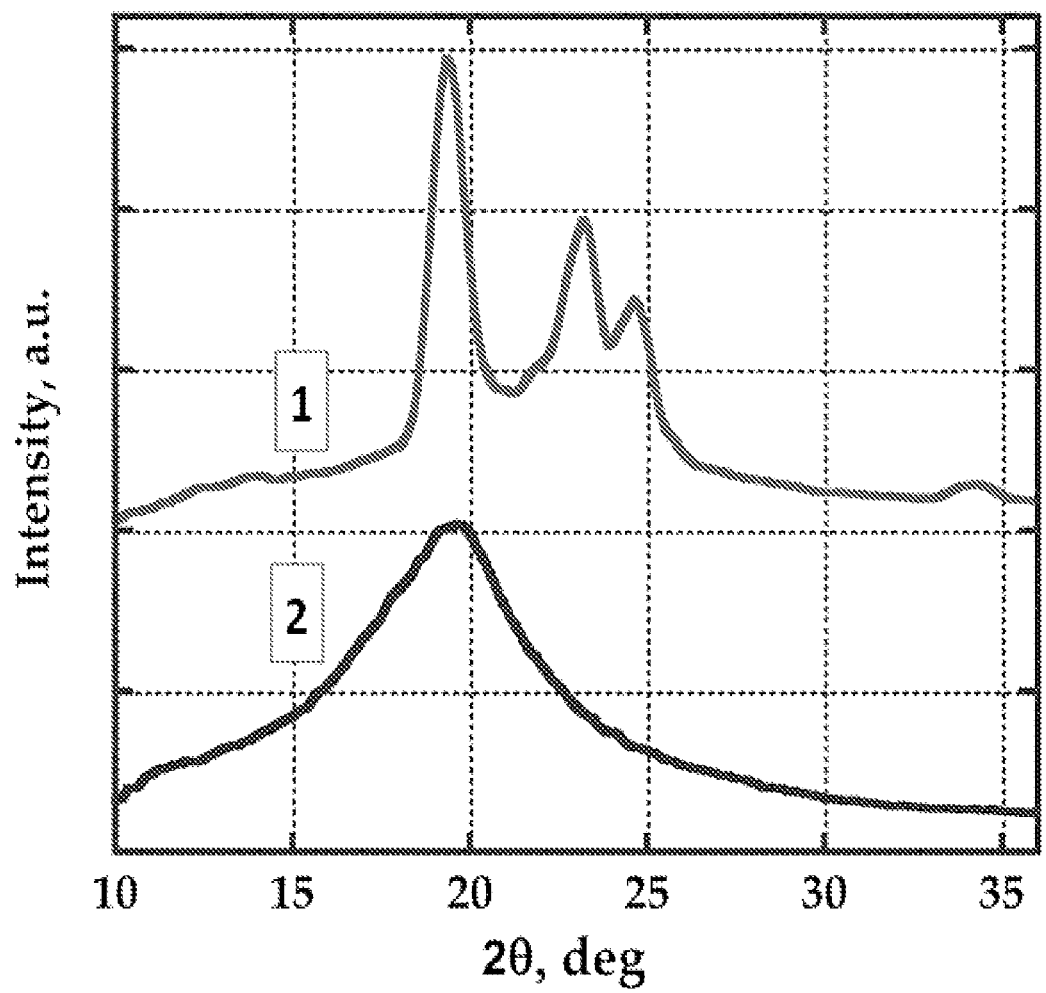
FIG. 2. A graph showing the X-ray diffraction patterns of pure eicosane at 20° C. (1) and at 60° C.
Figure 3:
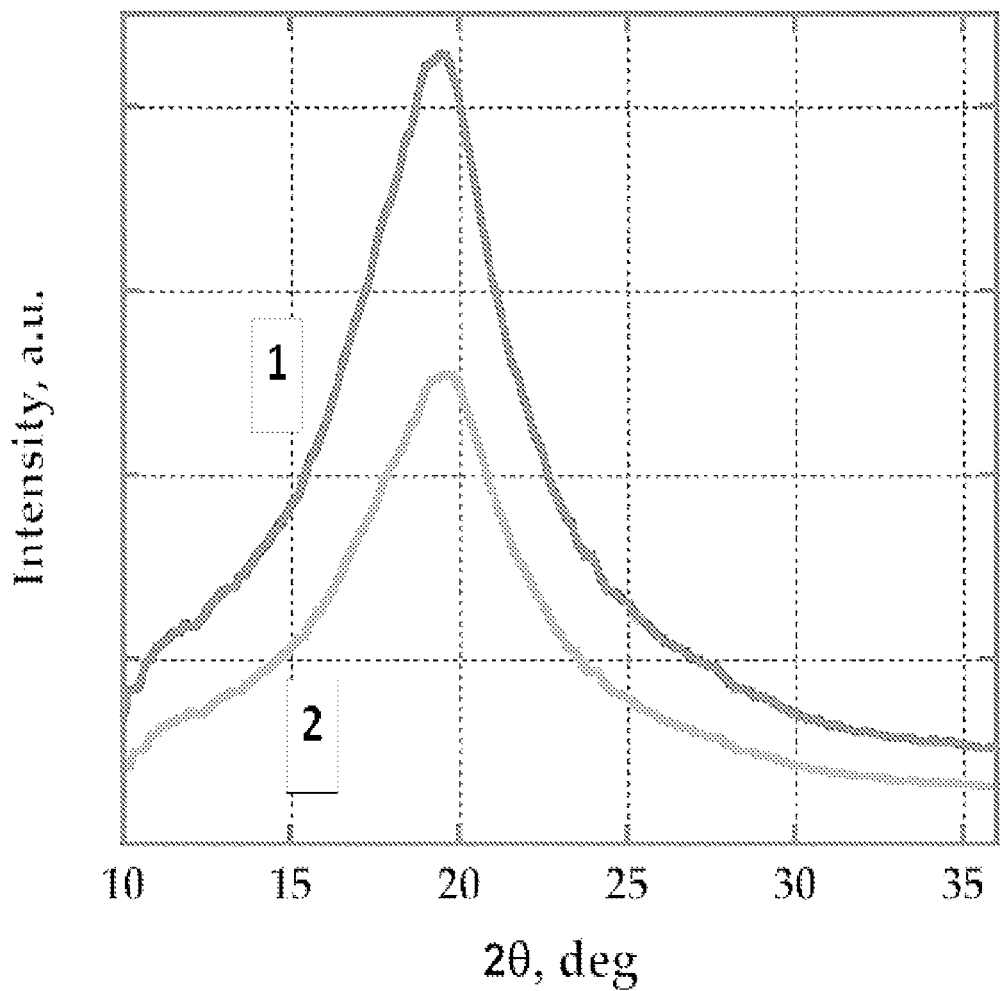
FIG. 3. A graph showing the X-ray diffraction patterns of dried eicosane/cellulose dispersion (1) and pure eicosane (2) at 60° C.
Figure 4:
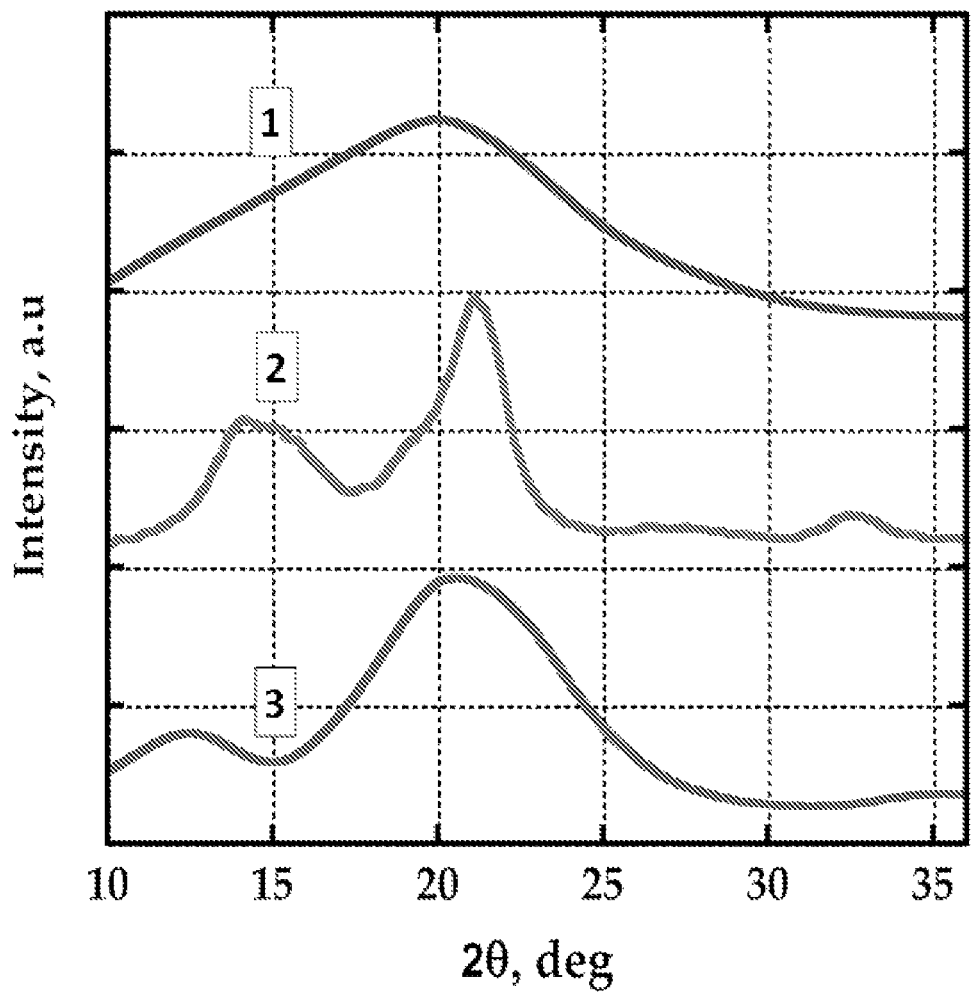
FIG. 4. A graph showing the X-ray diffraction patterns of amorphous cellulose, maid following [R. Avolio, I. Bonadies, D. Capitani, M. E. Errico, G. Gentile, M. Avella Carbohydrate Polymers 87 (2012) 265] (1), initial microcrystal cellulose (crystalline cellulose I) (2) and crystalline cellulose II (3) [D. L. Kaplan, Biopolymers From Renewable Resources. Berlin, Springer Verlag, Berlin, 1998.]
Figure 14:
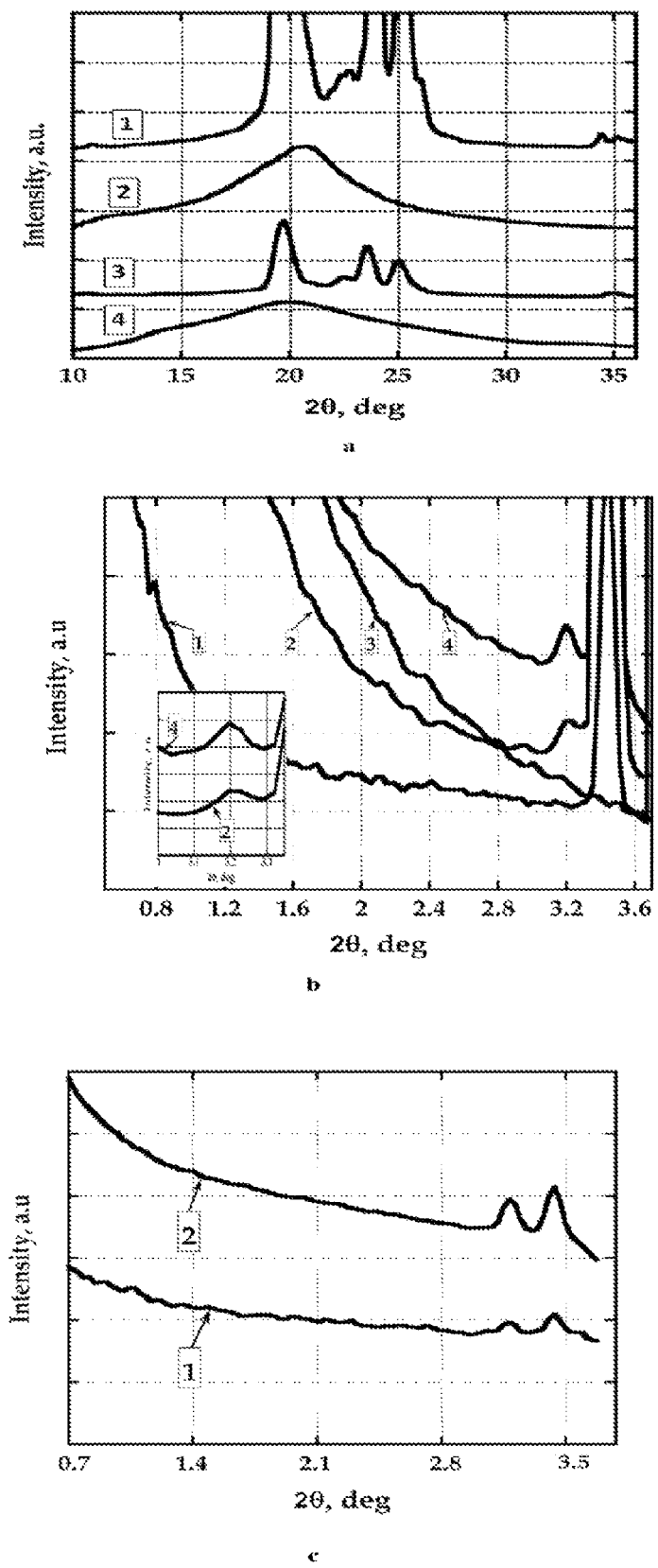
FIG. 14. Is a graph showing wide-angle (a) and small-angle (b, c) X-ray diffraction patterns from the dried and aqueous eicosane/cellulose (4:1) dispersions. In (a): pure eicosane at ambient temperature (1), dried dispersion, heated to 60° C. (2), dried dispersion at ambient temperature (3) and dried non-derivatized cellulose hydrogel (4). In (b): 1—pure eicosane, 2—dried dispersion, 3—pure microcrystal cellulose, 4—blown dispersion. In (c): 1-6 wt. % dispersion in IL/water (1:4) solution, 2-12 wt. % aqueous dispersion from the repeatedly dissolved solid dispersion.

An interesting observation can be seen in the small-angle diffraction patterns shown in FIGS. 14b and c. The sharp (002) reflection of the eicosane triclinic crystal in the bulk phase appears to have a weak satellite at somewhat smaller angles. This resembles the reported observation in graphite-intercalated eicosane, where it was assigned as the (02) reflection of an adsorbed phase exhibiting only two-dimensional lattice order. We suggest a similar interpretation in the present case, whereby the inner surface of the cellulose encapsulating layer interacts with adjacent eicosane molecules to induce the adsorbed phase. Surprisingly, the patterns from native and re-dissolved dispersions exhibit reflections from both types of crystals, but now with about comparable intensity. This indicates less-ordered packing of eicosane molecules in the encapsulated particles compared to the bulk phase, which is apparently due to the influence of the encapsulating cellulose. SAXS patterns measured from the eicosane/cellulose dispersion upon heating in the temperature range of 30 to 50° C., at steps of 5° C., indicate that both the triclinic bulk phase of the eicosane and the adsorbed phase melt together at about 37° C. This differs from the observations of n-alkanes in graphite, where the disordered phase was stable to significantly higher temperatures, and may be attributed to the weaker interaction between eicosane and the cellulose shell (see FIGS. 2-4).

Conclusions

The amphiphilic character of the cellulose chain can be exploited for formation of stable oil-in-water or water-in-oil dispersions. This may be done by mixing water, oil and cellulose solution in an ionic liquid. A more practical alternative is to form first a hydrogel from the cellulose/IL solution by coagulation with water and applying it to the sonicated water/oil or oil/water mixtures. We postulate that the dissolution/regeneration process affords higher mobility to the cellulose molecules so an encapsulating coating can be formed at the water-oil interface. Thus cellulose, due to its amphiphilic character, plays the role of a novel eco-friendly emulsifying agent. The dispersed particles described here exhibit a globular shape and dimensions around 200 nm for the main particle population, with some higher populations or aggregates. A solid-state dispersion is obtained by drying liquid dispersions of non-volatile compounds, and can be repeatedly dissolved in excess water to re-form a sustainable dispersion. At the final stage of drying, under reduced pressure, the dispersion can be blown, yielding a nanoporous foam (aerocellulose). The blowing agent can be either the residual water, or the entrapped hydrocarbon if volatile. The solid-state eicosane/cellulose dispersion as well as the aqueous dispersions possesses a very high effective heat-absorption capacity. X-ray diffraction patterns indicate that the encapsulating cellulose shell is indeed in the amorphous state. Small-angle diffraction patterns of eicosane dispersions exhibit two sharp reflections. One is due to the eicosane triclinic crystal bulk phase and the other at somewhat smaller angles is interpreted as due to less ordered phase, possibly due to interactions with the encapsulating cellulose.

Example 5: Enzymatic Hydrolysis of the Novel Cellulose Hydrogel Capsules

Solid-state dispersion included 10 wt. % of cellulose encapsulated neicosane (obtained according to method and procedure, discovered above) and was dissolved in water based acetic buffer (at 25° C.) with concentration of 50 mmol/L (pH-4.8) at weight ratio of 1:5.

The prepared dispersion was mixed at room temperature with a blend of commercial cellulolytic enzyme GC-220 (Genencor In., Danisco, N.Y., USA) and b-glucosidase Novozyme-188 (Novozymes A/S, Bagsvaerd, Denmark). The loading of GC-220 was 10 FPU per 1 g of pure cellulose and Novozyme-188 was 8 IU per 1 g of pure cellulose.

The kinetics of the cellulose hydrolysis were measured according to changes of the glucose concentration in the solution (which was tested by the conventional DNS-assay). The comparison with the hydrolysis kinetics of standard microcrystalline cellulose (Avicel, Sigma-Aldrich Ltd.) dispersion in the same enzymatic mixture showed more than hundredfold increase in hydrolysis speed of the present cellulose hydrogel capsules.

Example 6: Enzymatic Hydrolysis Properties of the Novel Cellulose Hydrogel Shell Encapsulated PCM Materials Liquid suspension included 10 wt. % of cellulose hydrogel encapsulated PCM based on n-eicosane core (obtained according to method and procedure as provided hereinabove) in water based acetic buffer with concentration of 50 mmol/L (pH~4.8) and was mixed with enzymatic blend as described in Example 5 at 55° C.

The suspension was quickly cooled to the surrounding temperature (25° C.) and measurement of cellulose hydrolysis kinetics was realized as described in Example 5. The comparison with the hydrolysis kinetics of standard microcrystalline cellulose dispersion in the same enzymatic mixture had shown more than 130-times increase of hydrolysis speed in favor of the present cellulose hydrogel encapsulated PCM.

What is claimed is:

1. A composition consisting of an interior hydrophobic space encapsulated by at least one non-derivatized cellulose molecular layer, wherein said cellulose is surrounded by a hydrophilic medium or a hydrophobic medium, wherein said composition: (a) is in the form of one or more particles, and (b) is devoid of a surfactant.

2. The composition of claim 1, comprising a cellulose hydrolyzing enzyme.

3. The composition of claim 1, wherein said cellulose is amorphic cellulose.

4. The composition of claim 1, wherein said cellulose is cellulose hydrogel.

5. The composition of claim 1, wherein said composition is oil-in-water composition.

6. The composition of claim 1, wherein said composition is water-in-oil composition.

7. The composition of claim 1, wherein said hydrophobic space or said hydrophobic medium comprises a hydrocarbon dispersion.

8. The composition of claim 1, wherein said hydrophilic medium is an aqueous medium or said hydrophilic space is an aqueous space.

9. The composition of claim 7, wherein said hydrocarbon dispersion comprises a polyglycol, an alkane, an alkene, an alkyne, an aromatic hydrocarbon, or any combination thereof.

10. The composition of claim 9, wherein said alkane is eicosane.

11. The composition of claim 1, wherein said composition is a capsule.

12. The composition of claim 11, wherein said capsule is 50-500 nm in diameter.

* * * * *